(12) United States Patent
Xu

(10) Patent No.: US 8,818,491 B2
(45) Date of Patent: Aug. 26, 2014

(54) SYSTEM FOR NON-CONTRAST ENHANCED MR ANATOMICAL IMAGING

(75) Inventor: Jian Xu, New Hyde Park, NY (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 740 days.

(21) Appl. No.: 13/019,379

(22) Filed: Feb. 2, 2011

(65) Prior Publication Data

US 2011/0263970 A1 Oct. 27, 2011

Related U.S. Application Data

(60) Provisional application No. 61/326,679, filed on Apr. 22, 2010, provisional application No. 61/326,677, filed on Apr. 22, 2010.

(51) Int. Cl.
| | |
|---|---|
| A61B 5/05 | (2006.01) |
| G01R 33/483 | (2006.01) |
| G01R 33/563 | (2006.01) |
| G01R 33/48 | (2006.01) |
| A61B 5/055 | (2006.01) |
| A61B 5/0402 | (2006.01) |
| G01R 33/567 | (2006.01) |
| G01R 33/561 | (2006.01) |

(52) U.S. Cl.
CPC ............ *A61B 5/055* (2013.01); *G01R 33/4833* (2013.01); *G01R 33/5635* (2013.01); *G01R 33/4822* (2013.01); *G01R 33/4835* (2013.01); *A61B 5/0402* (2013.01); *G01R 33/5673* (2013.01); *G01R 33/5617* (2013.01)
USPC .......................................... 600/419; 600/410

(58) Field of Classification Search
USPC ....................... 600/410, 413, 419
See application file for complete search history.

(56) References Cited

U.S. PATENT DOCUMENTS

| | | | |
|---|---|---|---|
| 5,857,970 A | * | 1/1999 | Purdy ........................... 600/413 |
| 6,144,201 A | | 11/2000 | Miyazaki |
| 6,801,800 B2 | | 10/2004 | Miyazaki et al. |

OTHER PUBLICATIONS

Co-pending U.S. Appl. No. 12/622,061, filed Nov. 19, 2009.
Neil M. Rofsky and Mark A Adelman, "MR Angiography in the Evaluation of Atherosclerotic Peripheral Vascular Disease", Radiology Feb. 2000—pp. 325-338.
Mitsue Miyazaki et al., "Non-contrast-Enhanced MR Angiography Using 3D ECG-Synchronized Half-Fourier Fast Spin Echo", Journal of Magnetic Resonance Imaging, 2000, pp. 776-783.
J.P. Mugler, "Practical Implementations of Optimized Tissue-Specific Prescribed Signal Evolutions for Improved Turbo-Spin-Echo Imaging", Proc. Intl. Soc. Mag. Reson. Med. 11 (2003).

(Continued)

*Primary Examiner* — Rajeev Siripurapu
(74) *Attorney, Agent, or Firm* — Peter R. Withstandley

(57) ABSTRACT

A system for Non-Contrast Agent enhanced MR imaging, includes an MR image acquisition device that acquires first and second datasets representing first and second image slabs individually comprising multiple image slices acquired at fast and slow blood flow portions of a heart cycle and oriented substantially perpendicular in at least one axis to direction of vasculature blood flow, in response to a heart cycle synchronization signal. An image data processor processes imaging datasets representing the first and second image slabs to provide first and second volume datasets representing a 3D volume imaged at the fast blood flow portion and the slow blood flow portion respectively and for providing a difference dataset representing an image difference between the first and second volume datasets and enhancing arterial blood flow. A display processor provides data representing an image showing the enhanced arterial blood flow.

28 Claims, 12 Drawing Sheets

(56) References Cited

OTHER PUBLICATIONS

Mitsue Miyazaki et al., "Peripheral MR Angiography: Separation of Arteries from Veins with Flow-spoiled Gradient Pulses in Electrocardiography-triggered Three-dimensional Half-Fourier Fast Spin-Echo Imaging", Radiology, Jun. 2003, pp. 890-896.

Jian Xu, et al., "Non-Contrast Time Resolved Pulmonary MRA with ECG-Triggered 3D Haste", ISMRM Abstract, Published 2005, Radiology 2003.

J. Xu, et al., "Reduced Acquisition Window with Parallel Technique Improves Non Contrast 3D HASTE MRA Imaging", Proc. Intl. Soc. Mag. Reson. Med 14 (2006).

M. Yui, et al., Aortic Arch to Intracranial 3D MRA with t-SLIT 3D-SSFP using a Neurovascular-Attached QD head SPEEDER Coil, Proc. Intl. Soc. Mag. Reson. Med. 11 (2004), 1 page.

* cited by examiner frequency-encoding

Prior Art

SYSTEM FOR NON-CONTRAST ENHANCED MR ANATOMICAL IMAGING

This is a non-provisional application of provisional application Ser. No. 61/326,679 filed 22 Apr. 2010 and Ser. No. 61/326,677 filed 22 Apr. 2010 by J. Xu.

FIELD OF THE INVENTION

This invention concerns a system for Non-Contrast Agent enhanced MR (magnetic resonance) imaging, by acquiring image slices oriented substantially perpendicular to direction of vasculature blood flow, at a relatively fast blood flow portion of a heart cycle and at a relatively slow blood flow portion of the heart cycle and by determining a difference between the slices.

BACKGROUND OF THE INVENTION

Known systems employ ECG-gated (Turbo) spin echo (TSE) imaging for MR Angiography using an intrinsic contrast mechanism by exploiting differences in the velocity of arterial blood during a cardiac cycle. In this type of imaging, an MR signal from stationary tissue and non-pulsatile venous blood is canceled by image subtraction, while an MR signal from arterial blood is preserved. This is because, faster flowing blood has a low MR signal on TSE images due to dephasing effects, while slow flowing blood has a higher signal. Known systems acquire two datasets during diastolic and systolic cardiac phase as illustrated in FIG. 1 corresponding to fast and slow flow periods of the cardiac cycle using ECG triggering. The datasets are subtracted and post processed using maximum intensity projection (MIP). The known systems employ readout methods including SPACE based readout (using a variable flip angle method) and Turbo Spin Echo readout including HASTE (Half Fourier Acquisition STE) as identified in FIG. 2.

The readout direction of known systems for limb imaging, for example, is along the direction of blood flow i.e. longitudinally along a limb as illustrated in FIG. 3 because this is the longest dimension of the anatomy and ensures efficient data acquisition. In order to obtain adequate recovery of magnetization between successive RF (radio frequency) excitation pulses, data is typically collected in one or more cardiac cycles. Many k-space lines (typically k-space lines of an entire slice (partition)) need to be collected per echo train to image a 3D volume within a reasonable scan time as illustrated in FIG. 4. Specifically, FIG. 4 illustrates acquisition of a slice every two heart cycles. Further, in order to achieve a larger field of view (FOV) coverage, known MR systems typically use a coronal orientation together with a localization scan to find vessels prior to an MRA scan which is time-consuming and operator dependent.

In known MR imaging systems, an entire 3D volume is excited with RF excitation fields over multiple cardiac cycles and typically two 3D datasets are acquired with one being acquired during a fast blood flow (e.g. systolic) cardiac period and another being acquired during a slow blood flow (diastolic) cardiac period. For example, known system perform imaging using a single shot SPACE or TSE sequence, with 80 partitions (slices) for 3D volume imaging, triggered by an RR waveform so that 160 RRs are needed, which is time consuming and therefore sensitive to respiratory motion disturbance. A system according to invention principles addresses the deficiencies of known MR imaging systems and related problems.

SUMMARY OF THE INVENTION

A system provides user friendly MR device operation with ECG triggering and Spin Echo sequence based Non Contrast Enhanced MR Angiography using transversal orientation acquisition and continuous patient table or electronic FOV movement to accelerate 3D image volume acquisition. A system for Non-Contrast Agent enhanced MR imaging, includes an MR image acquisition device. The MR image acquisition device acquires over multiple heart cycles, first and second datasets representing first and second image slabs individually comprising multiple image slices oriented substantially perpendicular in at least one axis to direction of vasculature blood flow, in response to a heart cycle synchronization signal. Within an individual heart cycle, a slice of a first image slab and a slice of a second image slab are acquired with one slice of one slab being acquired at a relatively fast blood flow portion of the heart cycle and the other slice of the other slab being acquired at a relatively slow blood flow portion of the heart cycle. An image data processor processes imaging datasets representing the first and second image slabs to provide first and second volume datasets representing a 3D volume imaged at the fast blood flow portion and the slow blood flow portion respectively and for providing a difference dataset representing an image difference between the first and second volume datasets and enhancing arterial blood flow. A display processor provides data representing an image showing the enhanced arterial blood flow.

DETAILED DESCRIPTION OF THE INVENTION

Definitions

An inversion recovery (IR) pulse inverts longitudinal magnetization from the positive z-axis by 180 degrees to the negative z-axis. IR pulses are used as preparation pulses prior to a main imaging pulse sequence to achieve different kinds of MR contrast (such as T1 weighted, T2 weighted). Adiabatic IR pulses are used to give more uniform contrast throughout an imaging volume than non-adiabatic RF pulses.

iPAT (integrated Parallel Acquisition Techniques) comprises "parallel imaging". It enables faster scanning through reduced phase encoding and addition of RF coil information. An iPAT factor of 2 enables scanning about twice as fast, iPAT factor of 3 enables scanning about three times as fast and so on.

TI=inversion time, the time between an inversion recovery pulse and the next RF excitation pulse. TI determines the image contrast.

$T_1$=the longitudinal (or spin-lattice) relaxation time $T_1$ decay constant.

$T_2$=the transverse (or spin-spin) relaxation time $T_2$ is the decay constant for a proton spin component.

TR=repetition time, the time between successive RF excitation pulses.

FA=flip angle, i.e., an RF flip angle. For an inversion pulse, FA=180 degrees.

Figure 6:
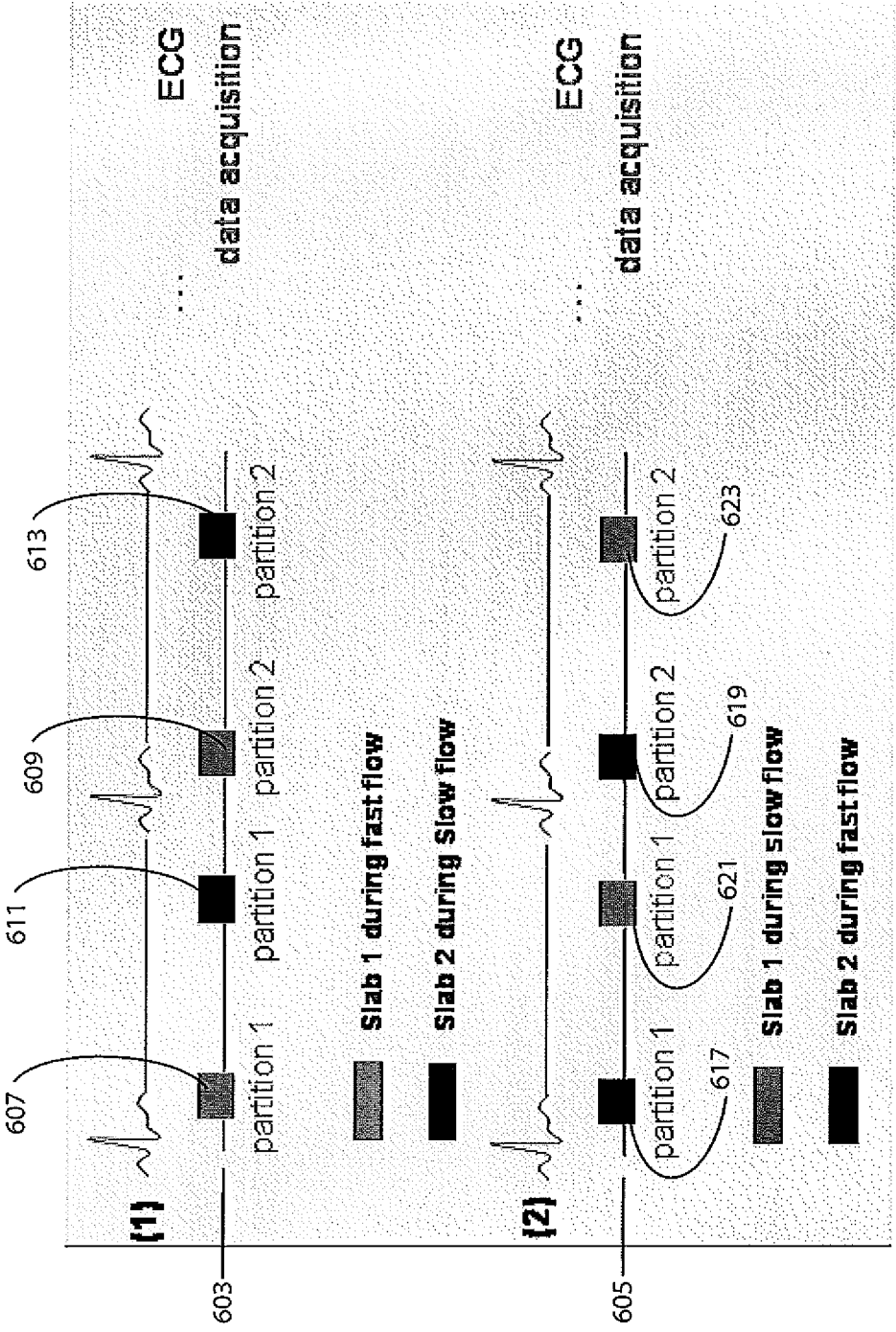
FIG. 6 shows an acquisition sequence employed by the system for acquisition of first and second slab image data in fast flow and slow flow periods, according to invention principles.

A system according to invention principles advantageously acquires a 3D imaging volume over multiple cardiac cycles by acquiring first and second image slices within individual heart cycles of the multiple heart cycles in response to a heart cycle synchronization signal. FIG. 6 shows acquisition sequences 603 and 605 employed by the system for acquisition of first and second slab image data in fast flow and slow flow periods. A 3D volume (80 slices) is divided into first and second slabs acquired by sequences 603 and 605, each comprising 40 slices. In sequence 603 a first slab comprises 20 slices, for example, including first, second . . . twentieth. slices (including slices 607, 609) acquired at a relatively fast blood flow (e.g. systolic) portion of a cycle and in sequence 605 the first slab comprises 20 slices, for example, including first, second . . . twentieth. slices (including slices 621, 623) acquired at a relatively slow blood flow (e.g. diastolic) portion of a cycle. Similarly, in sequence 603 a second slab comprises 20 slices, for example, including first, second . . . twentieth. slices (including slices 611, 613) acquired at a relatively slow blood flow (e.g. diastolic) portion of a cycle and in sequence 605 the second slab comprises 20 slices, for example, including first, second . . . twentieth. slices (including slices 617, 619) acquired at a relatively fast blood flow (e.g. systolic) portion of a cycle. The system acquires a slice for slab 1 and a slice for slab 2 in a single cardiac cycle. The system acquires two 3D slabs in 40 heart cycles (RR (R wave to R wave) intervals). The system employs a total number of 80 heart cycles using two slab RF excitation and the system advantageously halves the time required for acquisition and reduces sensitivity to respiratory motion. The fast and slow datasets are subtracted and post-processed using maximum intensity projection (MIP) to provide images with enhanced vasculature visualization. The system provides user friendly MR device operation with ECG triggered and Spin Echo sequence based Non Contrast Enhanced MR Angiography using transversal orientation acquisition and continuous patient table or electronic FOV movement to accelerate 3D image volume acquisition.

Figure 7:
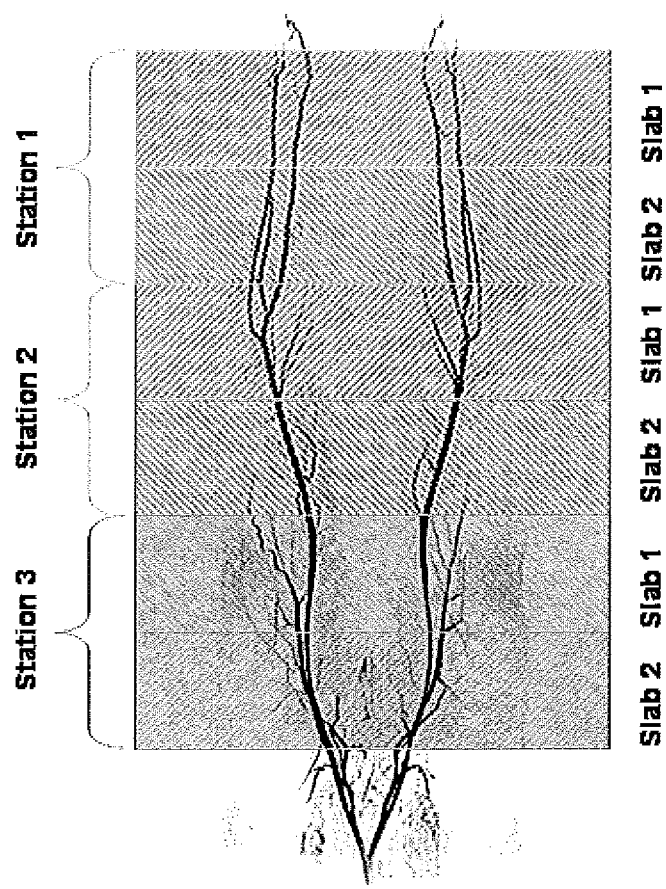
FIG. 7 illustrates MR image data acquisition at three stations using transversal orientation acquisition, according to invention principles
Figure 10:
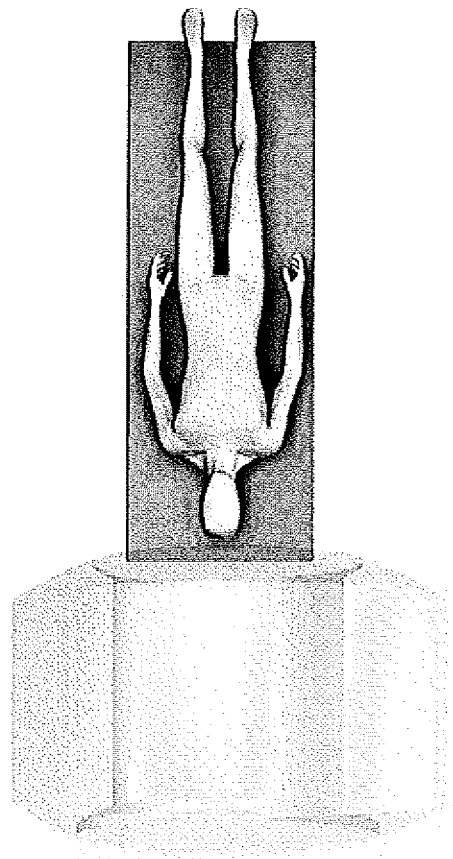
FIG. 10 illustrates positioning a patient table for automatically advancing through an MR imaging device, according to invention principles.

FIG. 7 illustrates MR image data acquisition at three stations (station 1, station 2 and station 3) using transversal orientation acquisition. The system performs multi-station MR Angiography acquisition of a whole peripheral vessel tree by advantageously automatically performing continuous patient table movement. FIG. 10 illustrates positioning a patient table for advancing through an MR imaging device. Alternatively, instead of (or as well as) moving a patient table, the system electronically shifts a field of view (FOV) in another embodiment. The system employs coronal, sagittal or transversal orientated 3D imaging. The multi-station interleaved two-slab acquisition further speeds up image data acquisition time. In FIG. 7, for individual stations 1, 2 and 3, a first slab (slab 1) is acquired during a fast blood flow period, and a second slab (slab 2) is acquired during a slow blood flow period. In response to completion of image data acquisition for a whole 3D volume comprising stations 1, 2 and 3, the system swaps the acquisition order and acquires slab 1 during slow blood flow period and acquires slab 2 during a fast blood flow period. The system advantageously reduces the total scan time by a factor 2. The system also advantageously uses transversal orientation 3D acquisition (substantially perpendicular to the blood flow direction) where the phase encoding direction is A-P (Anterior-Posterior), the 3D encoding direction is F-H (Foot-Head), frequency encoding direction is R-L (Right-Left).

Figure 1:
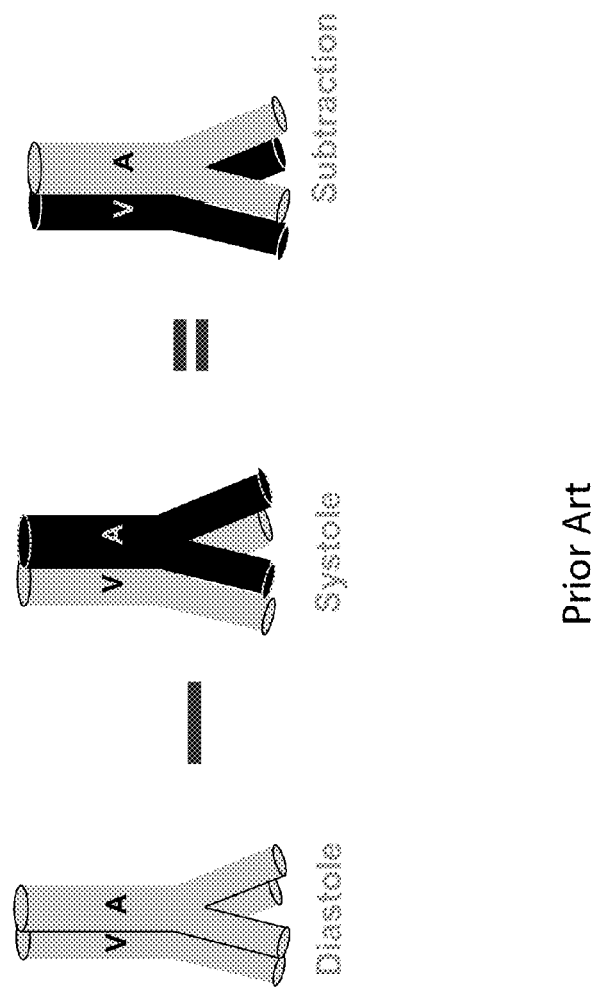
FIG. 1 illustrates a known system for processing two datasets for MR Angiography.
Figure 2:
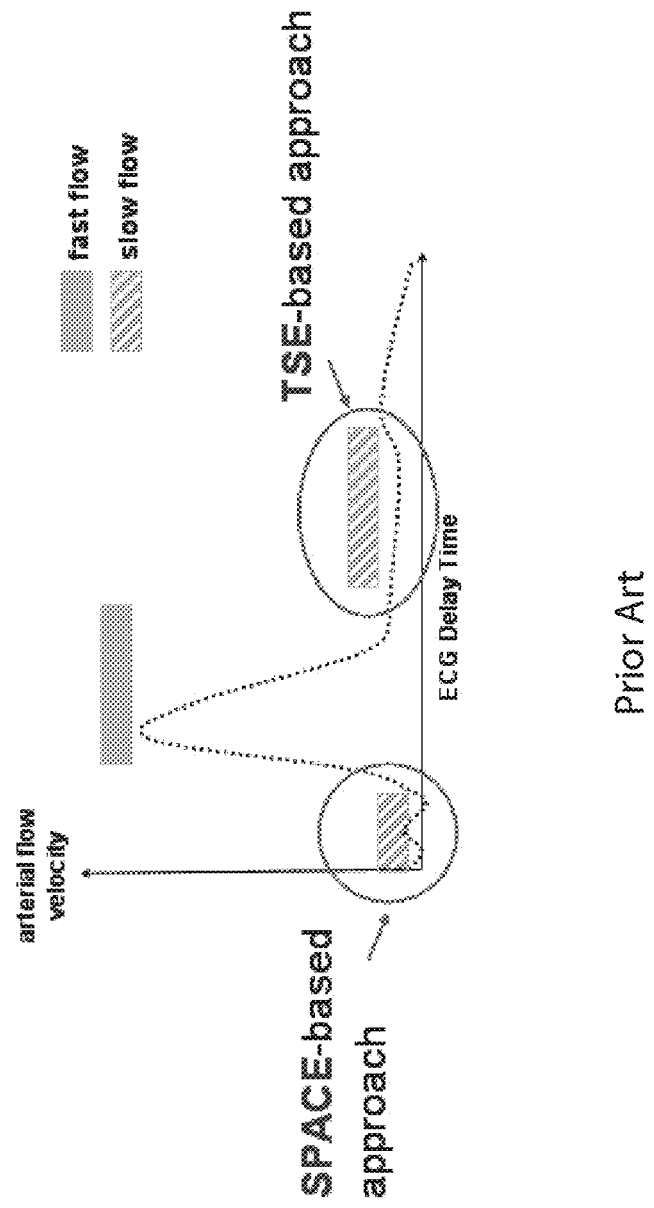
FIG. 2 illustrates known MR readout approaches for acquiring two datasets for MR Angiography.
Figure 3:
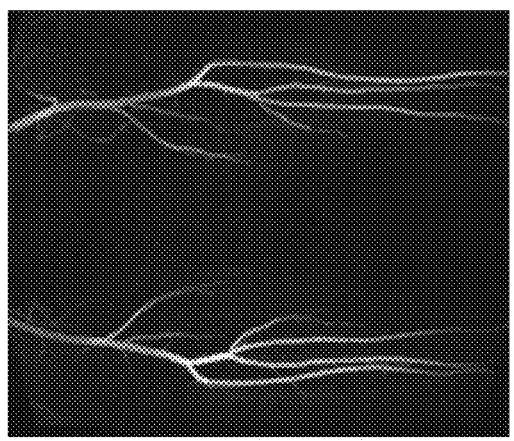
FIG. 3 illustrates known MR Angiography system readout direction is along the direction of flow.
Figure 4:
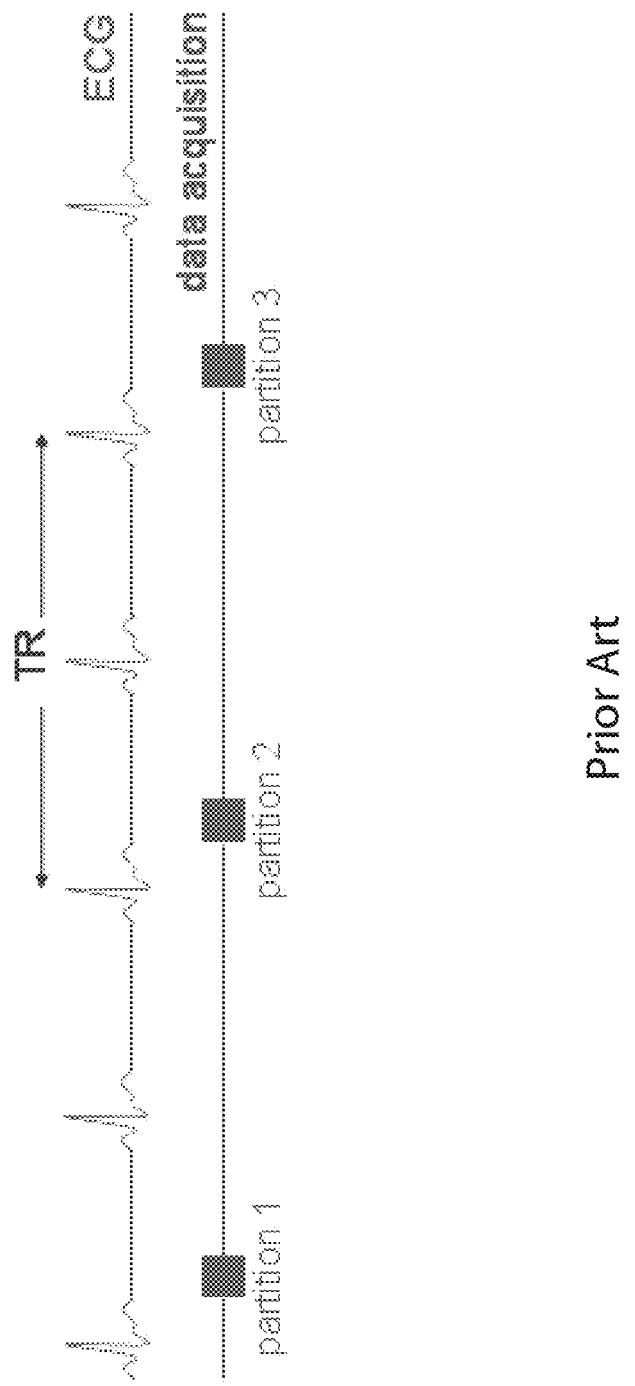
FIG. 4 illustrates a known MR Angiography acquisition sequence indicating adequate recovery of magnetization between successive excitations is achieved over one or more cardiac cycles.
Figure 5:
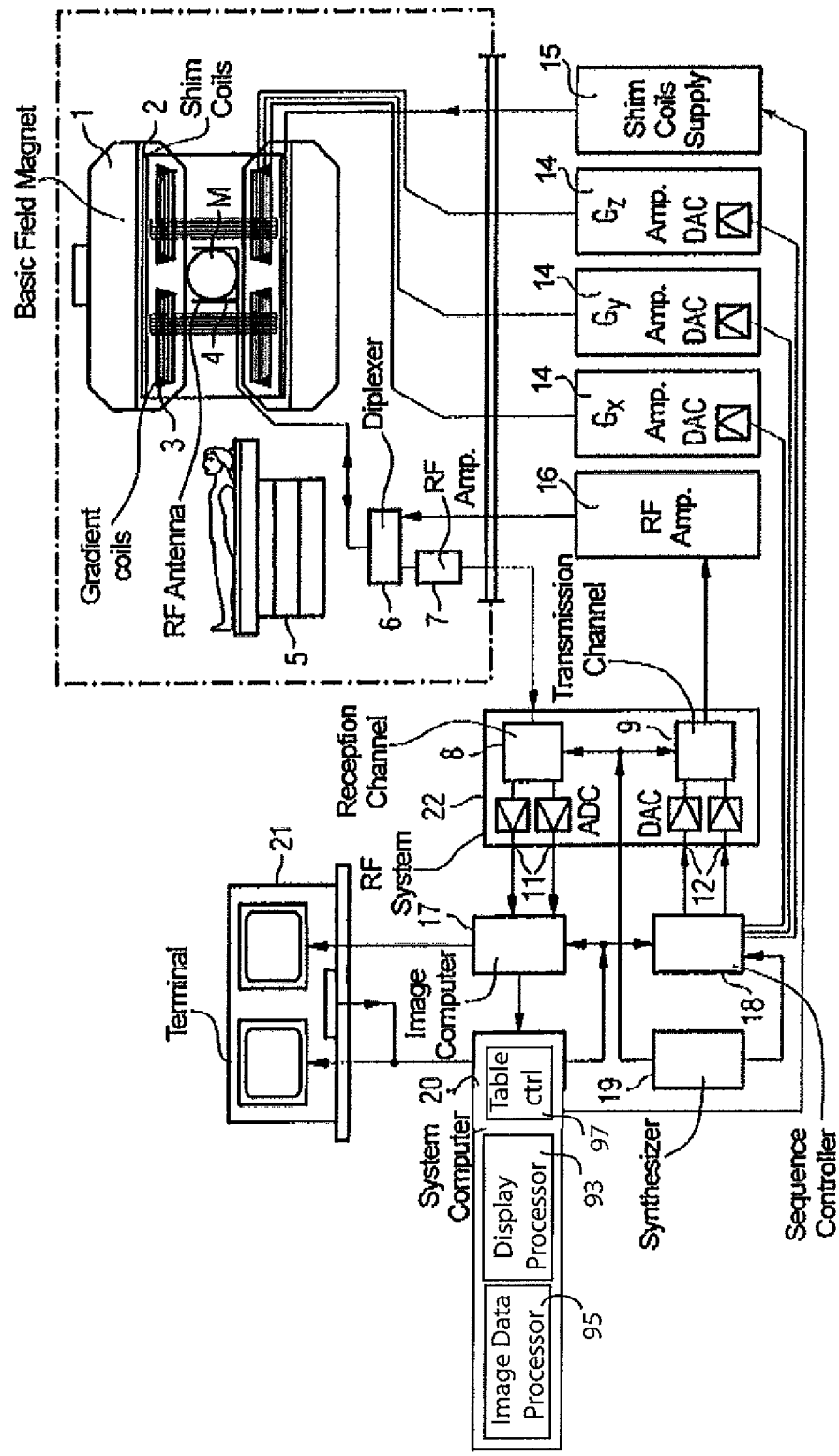
FIG. 5 shows a system for Non-Contrast Agent enhanced MR imaging, according to invention principles.

FIG. 5 shows system 10 for Non-Contrast Agent enhanced MR imaging. In system 10 a basic field magnet 1 generates a strong magnetic field, which is constant in time, for the polarization or alignment of the nuclear spins in the examination region of an object, such as, for example, a part of a human body to be examined. The high homogeneity of the basic magnetic field required for the magnetic resonance measurement is provided in a spherical measurement volume M, for example, into which the parts of the human body to be examined are brought. In order to satisfy the homogeneity requirements and especially for the elimination of time-invariant influences, shim-plates made of ferromagnetic material are mounted at suitable positions. Time-variable influences are eliminated by shim coils 2, which are controlled by a shim-current supply 15.

In the basic magnetic field 1, a cylinder-shaped gradient coil system 3 is used, which consists of three windings, for example. Each winding is supplied with current by an amplifier 14 in order to generate a linear gradient field in the respective directions of the Cartesian coordinate system. The first winding of the gradient field system 3 generates a gradient $G_x$ in the x-direction, the second winding generates a gradient $G_y$ in the y-direction, and the third winding generates a gradient $G_z$ in the z-direction. Each amplifier 14 contains a digital-analog converter, which is controlled by a sequence controller 18 for the generation of gradient pulses at proper times.

Within the gradient field system 3, radio-frequency (RF) coils 4 are located which convert the radio-frequency pulses emitted by a radio-frequency power amplifier 16 via multiplexer 6 into a magnetic alternating field in order to excite the nuclei and align the nuclear spins of the object to be examined or the region of the object to be examined. In one embodiment, RF coils 4 comprise a subset or substantially all of, multiple RF coils arranged in sections along the length of volume M corresponding to the length of a patient. Further, an individual section RF coil of coils 4 comprises multiple RF coils providing RF image data that is used in parallel to generate a single MR image. RF pulse signals are applied to RF coils 4, which in response produces magnetic field pulses which rotate the spins of the protons in the imaged body by ninety degrees or by one hundred and eighty degrees for so-called "spin echo" imaging, or by angles less than or equal to 90 degrees for so-called "gradient echo" imaging. In response to the applied RF pulse signals, RF coils 4 receive MR signals, i.e., signals from the excited protons within the body as they return to an equilibrium position established by the static and gradient magnetic fields. The MR signals comprising nuclear spin echo signals received by RF coils 4 as an alternating field resulting from the processing nuclear spins, are converted into a voltage that is supplied via an amplifier 7 and multiplexer 6 to a radio-frequency receiver processing unit 8 of a radio-frequency system 22.

The radio-frequency system 22 operates in an RF signal transmission mode to excite protons and in a receiving mode to process resulting RF echo signals. In transmission mode, system 22 transmits RF pulses via transmission channel 9 to initiate nuclear magnetic resonance in volume M. Specifically, system 22 processes respective RF echo pulses associated with a pulse sequence used by system computer 20 in conjunction with sequence controller 18 to provide a digitally represented numerical sequence of complex numbers. This numerical sequence is supplied as real and imaginary parts via digital-analog converter 12 in the high-frequency system 22 and from there to a transmission channel 9. In the transmission channel 9, the pulse sequences are modulated with a radio-frequency carrier signal, having a base frequency corresponding to the resonance frequency of the nuclear spins in the measurement volume M.

The conversion from transmitting to receiving operation is done via a multiplexer 6. RF coils 4 emit RF pulses to excite nuclear proton spins in measurement volume M and acquire resultant RF echo signals. The correspondingly obtained magnetic resonance signals are demodulated in receiver processing unit 8 of RF system 22 in a phase-sensitive manner, and are converted via respective analog-digital converters 11 into a real part and an imaginary part of the measurement signal and processed by imaging computer 17. Imaging computer 17 reconstructs an image from the processed acquired RF echo pulse data. The processing of RF data, the image data and the control programs is performed under control of system computer 20. In response to predetermined pulse sequence control programs, sequence controller 18 controls generation of desired pulse sequences and corresponding scanning of k-space. In particular, sequence controller 18 controls the switching of the magnetic gradients at appropriate times, transmission of RF pulses with a determined phase and amplitude and reception of magnetic resonance signals in the form of RF echo data. Synthesizer 19 determines timing of operations of RF system 22 and sequence controller 18. The selection of appropriate control programs for generating an MR image and the display of the generated nuclear spin image is performed by a user via terminal (console) 21, which contains a keyboard and one or more screens. System 10 uses magnetic field gradients and radio frequency excitation to create an image. System computer 20 translates acquired k-space data onto a Cartesian grid and a Three-Dimensional Fourier Transform (3DFT) method is used to process the data to form a final image. K-space is the temporary image space in which data from digitized MR signals is stored during data acquisition and comprises raw data in a spatial frequency domain before reconstruction. When k-space is full (at the end of an MR scan), the data is mathematically processed to produce a final image.

System computer 20 automatically (or in response to user command entered via terminal 21) employs and directs the MR imaging device of system 10 in Non-Contrast Agent enhanced MR imaging. The MR image acquisition device of system 10 acquires over multiple heart cycles, first and second datasets representing first and second image slabs individually comprising multiple image slices oriented substantially perpendicular in at least one axis, to direction of vasculature blood flow, in response to a heart cycle synchronization signal. Within an individual heart cycle a slice of a first image slab and a slice of a second image slab are acquired with one slice of one slab being acquired at a relatively fast blood flow portion of the heart cycle and the other slice of the other slab being acquired at a relatively slow blood flow portion of the heart cycle. Image data processor 95 in computer 20 processes imaging datasets representing the first and second image slabs to provide first and second volume datasets representing a 3D volume imaged at the fast blood flow portion and the slow blood flow portion respectively and for providing a difference dataset representing an image difference between the first and second volume datasets and enhancing arterial blood flow. Display processor 93 in computer 20 provides data representing an image showing the enhanced arterial blood flow. Patient support table controller 97 automatically advances a patient support table to change an imaged field of view in response to a pulse sequence used for image acquisition.

Figure 8:
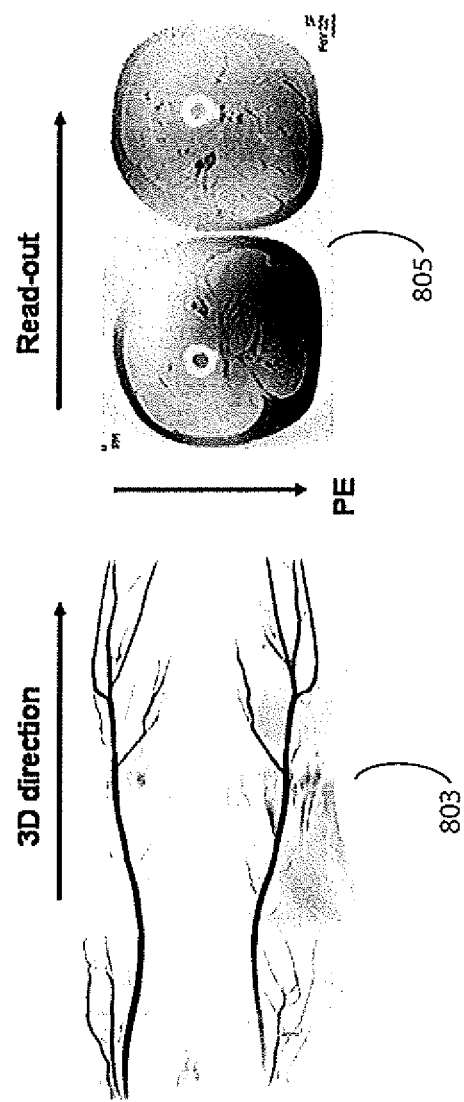
FIG. 8 illustrates MR transversal orientation data acquisition, according to invention principles.

FIG. 8 illustrates MR transversal orientation image data acquisition of a cross-section 805 of a patient limb 803. Successive cross-section images are acquired down the limb in accordance with the image acquisition timing sequences described herein. A rectangular FOV up to 35%-50% of the volume may be used and the Phase encoding (PE) direction is Anterior-Posterior of a limb in cross-section. A rectangular FOV is used to reduce the number of phase encoding lines acquired and reduce acquisition time, and is also advantageously used in particular cases to reduce T2 decay time, such as for a single shot EPI (Echo Planar Imaging) pulse sequence or a single shot TSE sequence, for example. System 10 uses a rectangular FOV (comprising the scanned region) in frequency and phase encoding directions and reduces the number of measurement lines acquired. A rectangular image is obtained because there are fewer rows than columns. System 10 reduces the FOV in the phase encoding direction (foldover direction) to reduce scan time by decreasing spatial resolution by undersampling.

Figure 9:
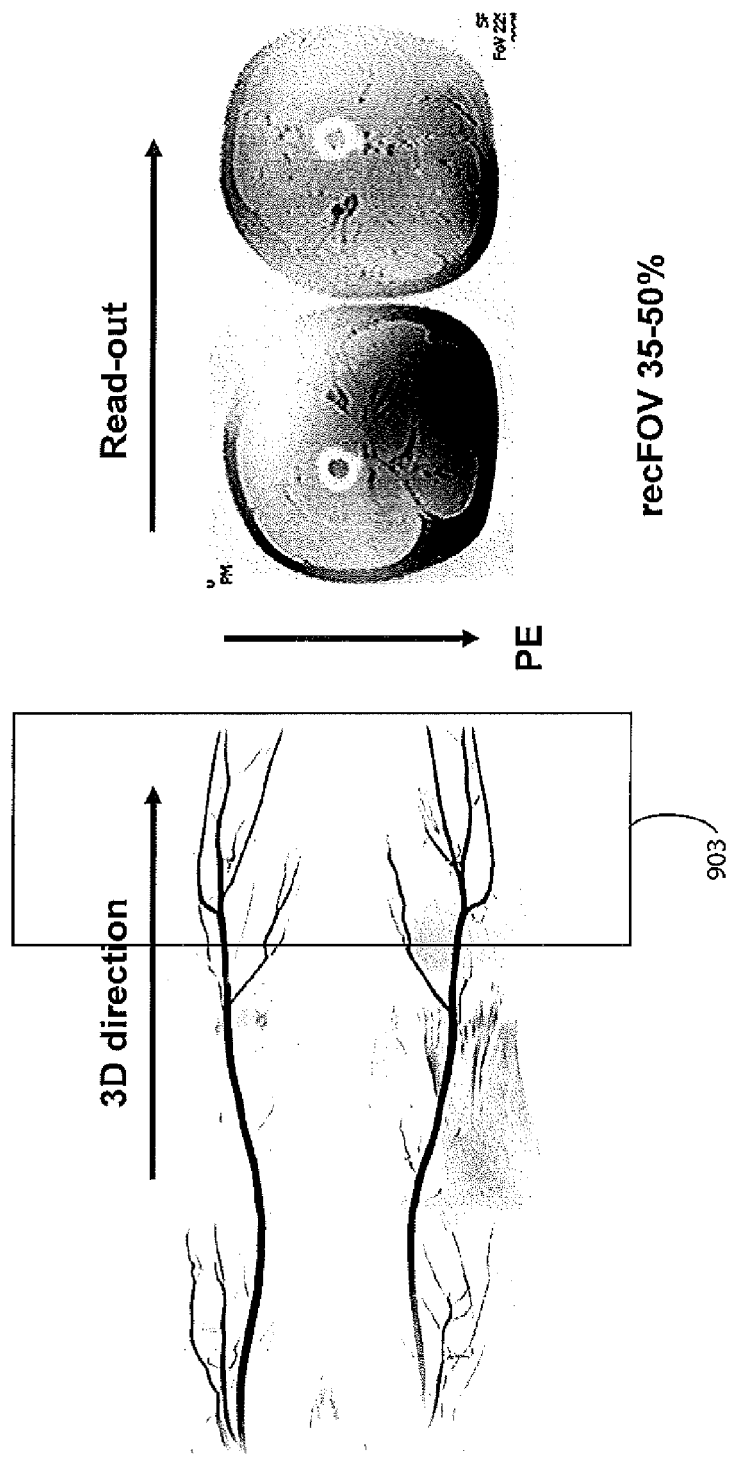
FIG. 9 illustrates MR transversal orientation data acquisition identifying a particular station, according to invention principles.

FIG. 9 illustrates MR transversal orientation data acquisition identifying a FOV 903. System 10 in one embodiment uses parallel imaging (SENSE or GRAPPA) in PE and 3D direction (along the limb) to accelerate imaging. In another embodiment system 10 employs a slice turbo factor and multiple slice acquisitions are performed for an individual RF pulse excitation. A rectangular FOV or integrated parallel imaging method (iPAT) is used in the PE direction to reduce the total image data acquisition time. Further, a scout sequence for imaging of peripheral limb arteries is not necessary since transversal orientation is used.

Figure 11:
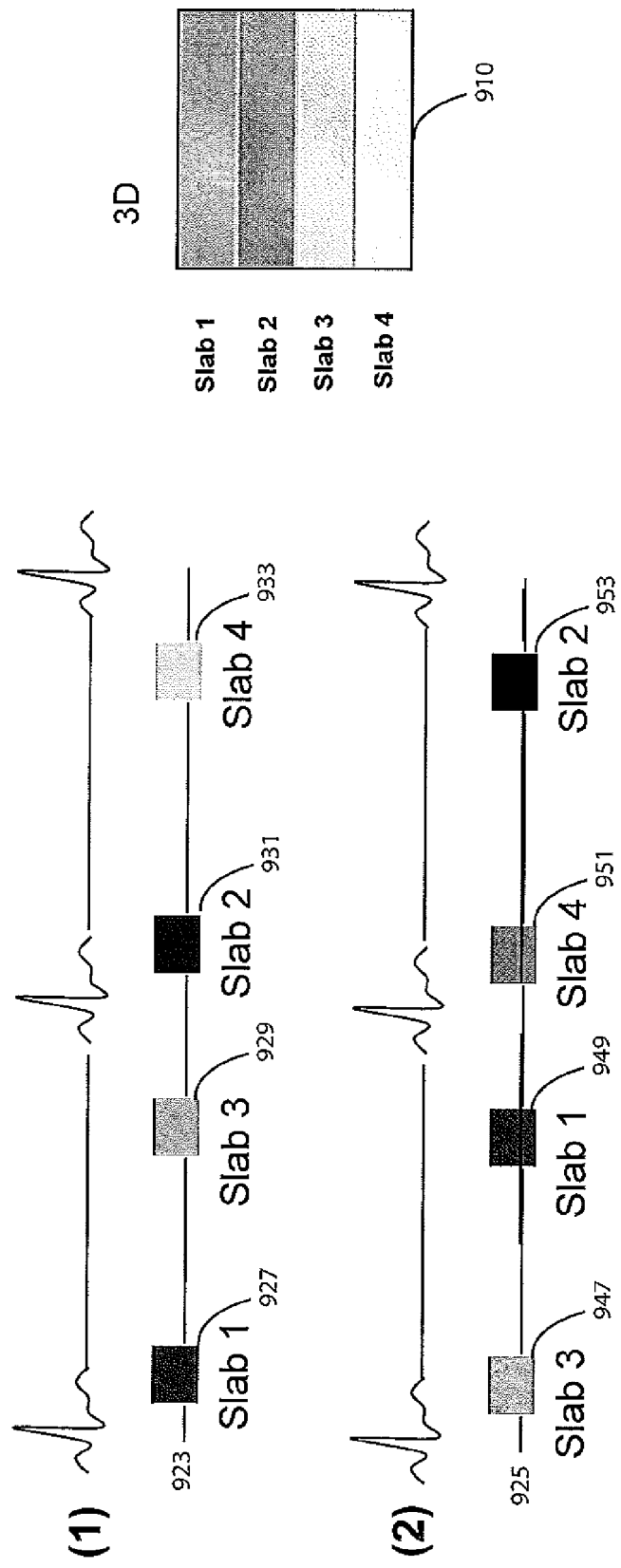
FIG. 11 shows an acquisition sequence employed by the system for acquisition of first, second, third and fourth slab image data in fast flow and slow flow periods to reduce cross-talk, according to invention principles.

FIG. 11 shows a pulse sequence employed by the system for acquisition of first, second, third and fourth slab image data in fast blood flow and slow blood flow periods to reduce cross-talk. Cross talk artifacts resulting from use of just two slabs per 3D imaging volume acquisition are reduced by using 4 slabs per 3D imaging volume, which also reduces image data acquisition time. FIG. 11 shows acquisition sequences 923 and 925 employed by the system for acquisition of first, second, third and fourth slab image data in fast flow and slow flow periods. A 3D volume 910 (80 slices) is divided into first, second third and fourth slabs acquired by sequences 923 and 925, each comprising 20 slices. In sequence 923, first and second slabs individually comprising 10 slices, including slices (partitions) 927, 931 are acquired at a relatively fast blood flow (e.g. systolic) portion of a cycle and third and fourth slabs individually comprising 10 slices, including slices (partitions) 929, 933 are acquired at a relatively slow blood flow (e.g. diastolic) portion of a heart cycle. Similarly, in sequence 925, first and second slabs individually comprising 10 slices, including slices (partitions) 949, 953 are acquired at a relatively slow blood flow (e.g. diastolic) portion of a cycle and third and fourth slabs individually comprising 10 slices, including slices (partitions) 947, 951 are acquired at a relatively fast blood flow (e.g. systolic) portion of a heart cycle.

System 10 (FIG. 5) acquires two slices for corresponding different slabs in a single cardiac cycle. The system acquires four 3D slabs in 40 heart cycles (RR (R wave to R wave) intervals). The system employs a total number of 80 heart cycles using four slab RF excitation and the system advantageously halves the time required for acquisition and reduces sensitivity to respiratory motion. The fast and slow datasets are subtracted and post processed using maximum intensity projection (MIP) to provide images with enhanced vasculature visualization. The system in this embodiment uses a repetition time (TR) comprising the time between successive RF excitation pulses of two heart cycles advantageously reducing cross talk relative to a two slab embodiment. The system provides user friendly MR device operation with ECG triggered and Spin Echo sequence based Non Contrast Enhanced MR Angiography using transversal orientation acquisition and continuous patient table or electronic FOV movement to accelerate 3D image volume acquisition. The system is also applicable for 2D imaging.

Figure 12:
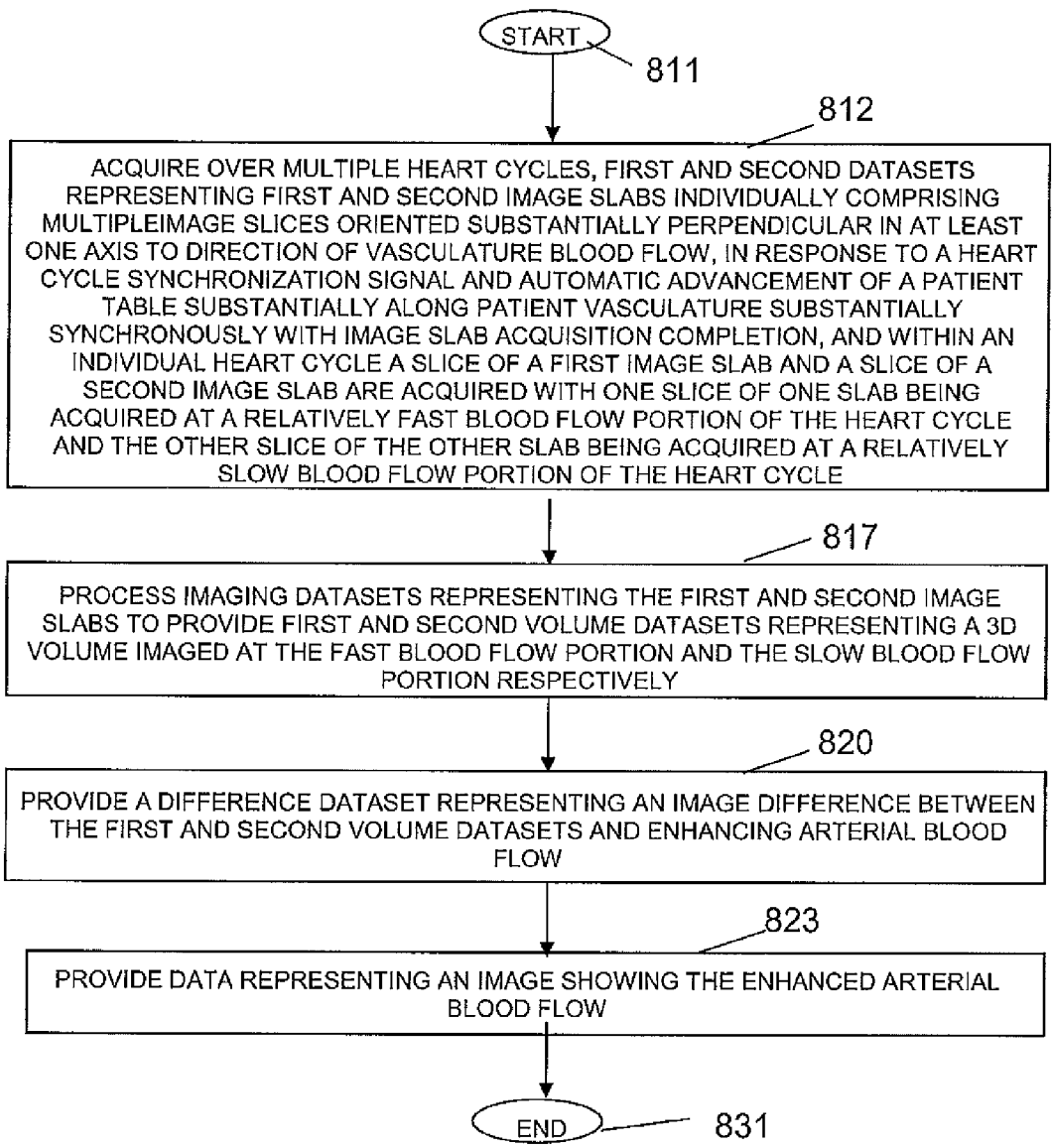
FIG. 12 shows a flowchart of a process performed by a system for Non-Contrast Agent enhanced MR imaging, according to invention principles.

FIG. 12 shows a flowchart of a process performed by system 10 (FIG. 5) for Non-Contrast Agent enhanced MR imaging. In step 812 following the start at step 811, the MR image acquisition device of system 10 acquires over multiple heart cycles, first and second datasets representing first and second image slabs individually comprising multiple image slices oriented substantially perpendicular in at least one axis to direction of vasculature blood flow, in response to a heart cycle synchronization signal and automatic advancement of a patient table substantially along patient vasculature substantially synchronously with image slab acquisition completion. Within an individual heart cycle a slice of a first image slab and a slice of a second image slab are acquired with one slice of one slab being acquired at a relatively fast blood flow portion of the heart cycle and the other slice of the other slab being acquired at a relatively slow blood flow portion of the heart cycle. The relatively fast flow portion of the heart cycle comprises a systolic portion and the relatively slow flow portion of the heart cycle comprises a diastolic portion. The first and second image slabs comprise adjacent respective first and second volumes encompassing a vessel structure of a patient and comprise a rectangular area.

In one embodiment, the MR image acquisition device alternates order of acquisition of the slice of the first image slab and the slice of the second image slab. The MR image acquisition device acquires first and second datasets representing first and second image slabs respectively using at least one of, a parallel imaging pulse sequence and a spin echo based pulse sequence. In one embodiment the spin echo based pulse sequence is a Turbo Spin Echo pulse sequence acquiring multiple slices per RF excitation. Further, in one embodiment, the MR image acquisition device alternates order of acquisition by acquiring slices of the first slab at the relatively fast blood flow portion of the heart cycle for a first portion of slices of the first slab and acquiring slices of the first slab at the relatively slow blood flow portion of the heart cycle for a second portion of slices of the first slab. Also, the MR image acquisition device alternates order of acquisition by acquiring slices of the second slab at the relatively fast blood flow portion of the heart cycle for a first portion of slices of the second slab and acquiring slices of the second slab at the relatively slow blood flow portion of the heart cycle for a second portion of slices of the second slab.

Patient support table controller 97 automatically advances the patient table substantially along patient vasculature to acquire image slabs substantially covering limb vasculature of a patient region of interest and synchronously with image acquisition. The acquired image slabs individually comprise multiple image slices oriented substantially perpendicular in at least one axis to direction of vasculature blood flow. In one embodiment, controller 97 automatically moves the patient table to acquire third and fourth image slabs substantially adjacent to the region comprising the first and second image slabs of a patient region of interest. The third and fourth image slabs individually comprise multiple image slices oriented substantially perpendicular in at least one axis to direction of vasculature blood flow. A region comprising the third and fourth image slabs overlaps a region comprising the first and second image slabs. In one embodiment, the MR image acquisition device automatically electronically advances a field of view substantially along patient vasculature to acquire image slabs substantially covering limb vasculature of a patient region of interest and synchronously with image acquisition. The acquired image slabs individually comprise multiple image slices oriented substantially perpendicular in at least one axis to direction of vasculature blood flow.

In step 817 image data processor 95 processes (e.g., by combining and subtracting) imaging datasets representing the first and second image slabs to provide first and second volume datasets representing a 3D volume imaged at the fast blood flow portion and the slow blood flow portion respectively. In step 820, processor 95 provides a difference dataset representing an image difference between the first and second volume datasets and enhancing arterial blood flow. Image data processor 95 provides the difference dataset using maximum intensity projection (MIP) processing and applies the maximum intensity projection (MIP) processing in saggital or coronal orientation to acquired datasets. Image data processor 95 combines image datasets representing the first and second image slabs to provide first and second volume datasets representing the 3D volume imaged at the fast blood flow portion and the slow blood flow portion respectively. In step 823 display processor 93 provides data representing an image showing the enhanced arterial blood flow. The process of FIG. 12 terminates at step 831.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. A user interface processor or generator is a known element comprising electronic circuitry or software or a combination of both for generating display images or portions thereof. A user interface comprises one or more display images enabling user A user interface (UI), as used herein, comprises one or more display images, generated by a user interface processor and enabling user interaction with a processor or other device and associated data acquisition and processing functions. The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 5-12 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system advantageously performs multi-stage transversal orientation MR Angiography image acquisition of a whole peripheral (e.g., limb) vessel tree by automatically advancing a patient table or by electronically shifting a field of view (FOV). Further, the processes and applications may, in alternative embodiments, be located on one or more (e.g., distributed) processing devices on a network linking the units of FIG. 5. Any of the functions and steps provided in FIGS. 5-12 may be implemented in hardware, software or a combination of both.

What is claimed is:

1. A system for Non-Contrast Agent enhanced MR imaging, comprising:
   an MR image acquisition device for acquiring over a plurality of heart cycles, first and second datasets representing first and second image slabs individually comprising a plurality of image slices oriented perpendicular in at least one axis to direction of vasculature blood flow, in response to a heart cycle synchronization signal, and within an individual heart cycle a slice of a first image slab and a slice of a second image slab are acquired with one slice of one slab being acquired at a relatively fast blood flow portion of said heart cycle and the other slice of the other slab being acquired at a relatively slow blood flow portion of said heart cycle;
   an image data processor for processing imaging datasets representing the first and second image slabs to provide first and second volume datasets representing a 3D volume imaged at said relatively fast blood flow portion and said relatively slow blood flow portion respectively and for providing a difference dataset representing an image difference between the first and second volume datasets and enhancing visibility of arterial blood flow; and
   a display processor for providing data representing an image showing the enhanced arterial blood flow.

2. A system according to claim 1, including a patient support table controller for automatically moving a patient table to acquire third and fourth image slabs adjacent the region comprising said first and second image slabs of a patient region of interest, said third and fourth image slabs individually comprising a plurality of image slices oriented perpendicular in at least one axis to direction of vasculature blood flow.

3. A system according to claim 2, wherein
   a region comprising said third and fourth image slabs overlaps a region comprising said first and second image slabs.

4. A system according to claim 1, including a patient support table controller for automatically advancing a patient table in a direction relative to patient vasculature to acquire image slabs covering limb vasculature of a patient region of interest and synchronously with image acquisition, wherein acquired image slabs individually comprise a plurality of image slices oriented perpendicular in at least one axis to direction of vasculature blood flow.

5. A system according to claim 4, wherein said patient support table controller automatically advances a patient table in a direction relative to patient vasculature synchronously with image slab acquisition completion.

6. A system according to claim 1, wherein
   said first and second image slabs comprise a rectangular area.

7. A system according to claim 1, wherein
   said MR image acquisition device acquires first and second datasets representing first and second image slabs respectively using a parallel imaging pulse sequence.

8. A system according to claim 1, wherein
   said MR image acquisition device acquires first and second datasets representing first and second image slabs respectively using a spin echo based pulse sequence.

9. A system according to claim 8, wherein
   said spin echo based pulse sequence is a Turbo Spin Echo pulse sequence acquiring multiple slices per RF excitation.

10. A system according to claim 1, wherein said MR image acquisition device automatically electronically advances a field of view in a direction relative to patient vasculature to acquire image slabs covering limb vasculature of a patient region of interest and synchronously with image acquisition, wherein acquired image slabs individually comprise a plurality of image slices oriented perpendicular in at least one axis relative to a direction of vasculature blood flow.

11. A system according to claim 1, wherein
   said image data processor provides said difference dataset using maximum intensity projection processing.

12. A system according to claim 11, wherein
   said image data processor applies said maximum intensity projection processing in saggital or coronal orientation to acquired datasets.

13. A system according to claim 1, wherein
   said relatively fast flow portion of said heart cycle comprises a systolic portion and said relatively slow flow portion of said heart cycle comprises a diastolic portion.

14. A system according to claim 1, wherein
   said first and second image slabs comprise adjacent respective first and second volumes encompassing a vessel structure of a patient.

15. A system according to claim 14, wherein
said MR image acquisition device alternates an order of acquisition of said slice of said first image slab and said slice of said second image slab across a plurality of heart cycles.

16. A system according to claim 15, wherein
said MR image acquisition device alternates an order of acquisition by acquiring slices of the first slab at said relatively fast blood flow portion of said heart cycle for a first portion of slices of the first slab and acquiring slices of the first slab at said relatively slow blood flow portion of said heart cycle for a second portion of slices of the first slab.

17. A system according to claim 16, wherein
said MR image acquisition device alternates an order of acquisition by acquiring slices of the second slab at said relatively fast blood flow portion of said heart cycle for a first portion of slices of the second slab and acquiring slices of the second slab at said relatively slow blood flow portion of said heart cycle for a second portion of slices of the second slab.

18. A system according to claim 1, wherein
said image data processor combines imaging datasets representing the first and second image slabs to provide first and second volume datasets representing said 3D volume imaged at said relatively fast blood flow portion and said relatively slow blood flow portion respectively.

19. A system for Non-Contrast Agent enhanced MR imaging, comprising:
an MR image acquisition device for acquiring over a plurality of heart cycles, first and second datasets representing first and second image slabs individually comprising a plurality of image slices oriented perpendicular in at least one axis to direction of vasculature blood flow, in response to a heart cycle synchronization signal and automatic advancement of a patient table in a direction relative to patient vasculature synchronously with image slab acquisition completion, and within an individual heart cycle a slice of a first image slab and a slice of a second image slab are acquired with one slice of one slab being acquired at a relatively fast blood flow portion of said heart cycle and the other slice of the other slab being acquired at a relatively slow blood flow portion of said heart cycle;
an image data processor for processing imaging datasets representing the first and second image slabs to provide first and second volume datasets representing a 3D volume imaged at said relatively fast blood flow portion and said relatively slow blood flow portion respectively and for providing a difference dataset representing an image difference between the first and second volume datasets and enhancing visibility of arterial blood flow; and
a display processor for providing data representing an image showing the enhanced arterial blood flow.

20. A system according to claim 19, including
said relatively fast flow portion of said heart cycle comprises a systolic portion and said relatively slow flow portion of said heart cycle comprises a diastolic portion.

21. A method for Non-Contrast Agent enhanced MR imaging, comprising the activities of:
employing at least one processing device for,
acquiring over a plurality of heart cycles, first and second datasets representing first and second image slabs individually comprising a plurality of image slices oriented perpendicular in at least one axis to a direction of vasculature blood flow, in response to a heart cycle synchronization signal, and within an individual heart cycle a slice of a first image slab and a slice of a second image slab are acquired with one slice of one slab being acquired at a relatively fast blood flow portion of said heart cycle and the other slice of the other slab being acquired at a relatively slow blood flow portion of said heart cycle;
processing imaging datasets representing the first and second image slabs to provide first and second volume datasets representing a 3D volume imaged at said relatively fast blood flow portion and said relatively slow blood flow portion respectively and for providing a difference dataset representing an image difference between the first and second volume datasets and enhancing visibility of arterial blood flow; and
providing data representing an image showing the enhanced arterial blood flow.

22. A system for Non-Contrast Agent enhanced MR imaging, comprising:
an MR image acquisition device for acquiring over a plurality of heart cycles, first and second datasets representing first and second image slabs individually comprising a plurality of image slices, in response to a heart cycle synchronization signal, and within an individual heart cycle a slice of a first image slab and a slice of a second image slab are acquired with one slice of one slab being acquired at a relatively fast blood flow portion of said heart cycle and the other slice of the other slab being acquired at a relatively slow blood flow portion of said heart cycle;
an image data processor for using imaging datasets representing the first and second image slabs to provide first and second volume datasets representing a 3D volume imaged at said relatively fast blood flow portion and said relatively slow blood flow portion respectively and for providing a difference dataset representing an image difference between the first and second volume datasets and enhancing visibility of arterial blood flow; and
a display processor for providing data representing an image showing the enhanced arterial blood flow.

23. A system for Non-Contrast Agent enhanced MR imaging, comprising:
an MR image acquisition device for acquiring over a plurality of heart cycles, first and second datasets representing first and second image slabs individually comprising a plurality of image slices, in response to a heart cycle synchronization signal, and within an individual heart cycle a slice of a first image slab and a slice of a second image slab are acquired with one slice of one slab being acquired at a relatively fast blood flow portion of said heart cycle and the other slice of the other slab being acquired at a relatively slow blood flow portion of said heart cycle;
an image data processor for combining and subtracting imaging datasets representing the first and second image slabs to provide first and second volume datasets representing a 3D volume imaged at said relatively fast blood flow portion and said relatively slow blood flow portion respectively and for providing a difference dataset representing an image difference between the first and second volume datasets and enhancing visibility of arterial blood flow; and
a display processor for providing data representing an image showing the enhanced arterial blood flow.

24. A system according to claim 23, wherein
said relatively fast flow portion of said heart cycle comprises a systolic portion and said relatively slow flow portion of said heart cycle comprises a diastolic portion.

25. A system according to claim 23, wherein said first and second image slabs comprise adjacent respective first and second volumes encompassing a vessel structure of a patient.

26. A system according to claim 25, wherein said MR image acquisition device alternates order of acquisition of said slice of said first image slab and said slice of said second image slab across a plurality of heart cycles.

27. A system according to claim 26, wherein said MR image acquisition device alternates order of acquisition by acquiring slices of the first slab at said relatively fast blood flow portion of said heart cycle for a first portion of slices of the first slab and acquiring slices of the first slab at said relatively slow blood flow portion of said heart cycle for a second portion of slices of the first slab.

28. A system according to claim 27, wherein said MR image acquisition device alternates order of acquisition by acquiring slices of the second slab at said relatively fast blood flow portion of said heart cycle for a first portion of slices of the second slab and acquiring slices of the second slab at said relatively slow blood flow portion of said heart cycle for a second portion of slices of the second slab.

* * * * *